ated under 35

United States Patent
Martin-Portugues et al.

(10) Patent No.: US 8,338,530 B2
(45) Date of Patent: Dec. 25, 2012

(54) POLYISOCYANATES CONTAINING ALLOPHANATE GROUPS

(75) Inventors: Marta Martin-Portugues, Ludwigshafen (DE); Carl Jokisch, Mannheim (DE); Harald Schaefer, Mannheim (DE); Lydie Tuchbreiter, Speyer (DE); Angelika Maria Steinbrecher, Stuttgart (DE)

(73) Assignee: BASF SE, Ludwigshafen (DE)

( * ) Notice: Subject to any disclaimer, the term of this patent is extended or adjusted under 35 U.S.C. 154(b) by 234 days.

(21) Appl. No.: 12/743,583

(22) PCT Filed: Dec. 2, 2008

(86) PCT No.: PCT/EP2008/066612
§ 371 (c)(1),
(2), (4) Date: May 19, 2010

(87) PCT Pub. No.: WO2009/071533
PCT Pub. Date: Jun. 11, 2009

(65) Prior Publication Data
US 2010/0273938 A1    Oct. 28, 2010

(30) Foreign Application Priority Data
Dec. 6, 2007    (EP) .................... 07122511

(51) Int. Cl.
C08L 75/00    (2006.01)
C07C 265/00    (2006.01)
C08G 18/30    (2006.01)

(52) U.S. Cl. ............... 524/589; 560/357; 528/60

(58) Field of Classification Search ........... 524/589; 560/357; 528/60
See application file for complete search history.

(56) References Cited

U.S. PATENT DOCUMENTS

| | | | |
|---|---|---|---|
| 3,817,939 A | 6/1974 | Allen et al. | |
| 4,040,992 A | 8/1977 | Bechara et al. | |
| 4,160,080 A | 7/1979 | Koenig et al. | |
| 4,324,879 A | 4/1982 | Bock et al. | |
| 4,596,678 A | 6/1986 | Merger et al. | |
| 4,596,679 A | 6/1986 | Hellbach et al. | |
| 5,087,739 A | 2/1992 | Bohmholdt et al. | |
| 5,290,902 A | 3/1994 | Jacobs et al. | |
| 6,228,472 B1 * | 5/2001 | Tazzia | 428/413 |
| 6,392,001 B1 * | 5/2002 | Mertes et al. | 528/59 |
| 2002/0007036 A1 | 1/2002 | Bruchmann et al. | |
| 2005/0222365 A1 * | 10/2005 | Mager et al. | 528/73 |
| 2007/0218209 A1 | 9/2007 | Asahina et al. | |

FOREIGN PATENT DOCUMENTS

| | | |
|---|---|---|
| DE | 26 31 733 | 2/1977 |
| DE | 28 06 731 | 8/1979 |
| DE | 29 01 479 | 7/1980 |
| DE | 38 06 276 | 9/1989 |
| DE | 100 13 186 | 9/2001 |
| DE | 100 13 187 | 10/2001 |
| DE | 10 2004 015 982 | 10/2005 |
| DE | 10 2004 015 983 | 10/2005 |
| DE | 10 2004 015 985 | 10/2005 |
| EP | 0000194 | 1/1979 |
| EP | 0 010 589 | 5/1980 |
| EP | 0 126 299 | 11/1984 |
| EP | 0 126 300 | 11/1984 |
| EP | 0 355 443 | 2/1990 |
| EP | 1 134 247 | 9/2001 |
| EP | 1 721 920 | 11/2006 |
| GB | 994 890 | 6/1965 |

OTHER PUBLICATIONS

U.S. Appl. No. 12/744,395, filed May 24, 2010, Kutschera, et al.
U.S. Appl. No. 12/681,538, filed Apr. 2, 2010, Jokisch, et al.
U.S. Appl. No. 13/181,938, filed Jul. 13, 2011, Elizalde, et al.

* cited by examiner

*Primary Examiner* — Ling Choi
*Assistant Examiner* — Aiqun Li
(74) *Attorney, Agent, or Firm* — Oblon, Spivak, McClelland, Maier & Neustadt, L.L.P.

(57) ABSTRACT

Allophanate-group-containing polyisocyanates based on isophorone diisocyanate, represented by formula (I)

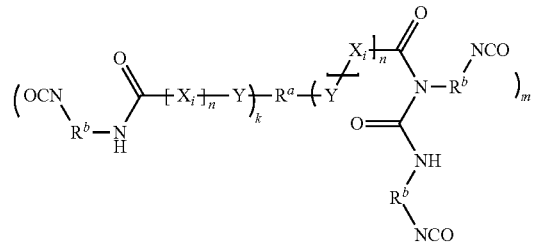

wherein $R^a$, k, m, (k+m), Y, $X_i$, n and $R^b$ are as defined, and to their use.

16 Claims, No Drawings

POLYISOCYANATES CONTAINING ALLOPHANATE GROUPS

The present invention relates to new, allophanate-group-containing polyisocyanates based on isophorone diisocyanate and to their use.

GB 994890 describes the preparation of allophanates from diisocyanates and monofunctional or polyfunctional alcohols, using metal carboxylates, metal chelates, and tertiary amines. Explicitly disclosed is the reaction of tolylene diisocyanate with trimethylolpropane and of isophorone diisocyanate with 1,6-hexanediol.

EP 194 A1 describes the preparation of allophanate-group-containing polyisocyanates from aliphatic or cycloaliphatic isocyanates by catalysis of acids. For this purpose, the starting compounds are preferably urethanes of phenolic polyhydroxy compounds, monohydric to tetrahydric aliphatic alcohols, monohydric to tetrahydric cycloaliphatic alcohols, monohydric to tetrahydric araliphatic alcohols, or higher molecular mass polyols. Diisocyanates specified for this reaction are aliphatic or cycloaliphatic diisocyanates or xylylene diisocyanates.

Explicitly disclosed by example 8 of EP 194 A1 is the formation of an allophanate-group-containing polyisocyanate by reaction of isophorone diisocyanate with 1,6-hexanediol and n-butanol, induced by hydrogen chloride.

Essential to the invention of EP 194 A1 is the use of strong protic acids as catalysts.

According to EP 194 A1, the metal carboxylates, metal chelates and tertiary amines already known from GB 994890 lead to considerable formation of dimeric and tertiary polyisocyanates, in addition to the desired formation of allophanate.

DE 102004015985 A1 describes the formation of allophanate prepolymers from isocyanates and polyether polyols having a molar weight of 300 to 20 000 and a functionality of more than 1.9. Preferred isocyanates are 1,6-hexamethylene diisocyanate and/or isophorone diisocyanate, and catalysts disclosed comprise Lewis acids or Brønsted acids.

All that are explicitly disclosed are products based on 1,6-hexamethylene diisocyanate with polyethers with a functionality of 2.

DE 102004015982 A1 describes the stabilization of allophanate prepolymers formed from isocyanates and polyhydroxy compounds.

All that are explicitly disclosed are products based on 1,6-hexamethylene diisocyanate with polyethers with a functionality of 2.

DE 102004015983 A1 describes the preparation of allophanate prepolymers from isocyanates and polyhydroxy compounds with an average functionality of >1.5 using a Zn catalyst.

All that are explicitly disclosed are products based on 1,6-hexamethylene diisocyanate with polyethers with a functionality of 2.

U.S. Pat. No. 5,290,902 discloses the preparation of mixtures of allophanates and isocyanurates in the ratio from 10:1 to 1:10, where, as alcohols, a description is given only of monoalcohols.

In spite of all of these compounds described in the prior art, there continues to be a need for high-functionality polyisocyanates of low viscosity.

It was an object of the present invention to provide new, high-functionality polyisocyanates for coating materials, especially for transparent coating materials, which have a high scratch resistance in conjunction with good elasticity.

The products ought also to have a low viscosity, to make them easier to incorporate into coating materials.

This object has been achieved by means of allophanate-group-containing polyisocyanates of the formula (I)

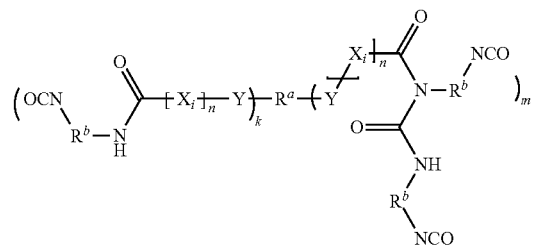

in which
$R^a$ is a (k+m)-valent radical, preferably an organic radical,
k is 0 or a positive number,
m is a positive number,
with the proviso that (k+m) together add up to a positive number of at least 3,
Y is an oxygen or a nitrogen atom,
$X_i$ for each i from 1 to n independently of one another is selected from the group consisting of —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O— und —CHPh-$CH_2$—O—, preferably from the group —$CH_2$—$CH_2$—O—, —$CH_2$—$CH(CH_3)$—O— and —$CH(CH_3)$—$CH_2$—O—, and more preferably —$CH_2$—$CH_2$—O—,
in which Ph is phenyl and Vin is vinyl,
n for each k and each m independently of one another is 0 or a positive number, and
$R^b$ for each k and each m independently of one another is a radical

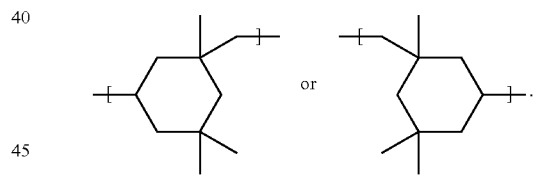

The parent alcohols of the allophanates of the invention are (k+m)-valent alcohols which may optionally carry groups $X_i$, in which (k+m), in accordance with the invention, is at least 3, preferably 3 to 6, more preferably 3 to 4, and very preferably 3.

The values for k, m, and n may on average adopt uneven values, but in that case are of course even relative to each individual molecule of the formula (I).

Preferably m>k, more preferably m≧(k+1), very preferably k≦0.5, more particularly k ≦0.2, and especially k=0.

These (k+m)-valent alcohols have a molecular weight of preferably below 500, more preferably below 400, very preferably below 350, more particularly below 300, and especially below 250 g/mol.

Examples of such alcohols $R^a$—(—Y—H)$_{(k+m)}$, in which Y is an oxygen atom, are trimethylolbutane, trimethylolpropane, trimethylolethane, pentaerythritol, glycerol, ditrimethylolpropane, dipentaerythritol, sorbitol, mannitol, diglycerol, threitol, erythritol, adonitol (ribitol), arabitol (lyxitol), xylitol or dulcitol (galactitol).

Preference is given to trimethylolpropane, pentaerythritol, glycerol, and diglycerol, preferably trimethylolpropane and glycerol, and more preferably trimethylolpropane.

In one embodiment of the present invention there are no groups $X_i$ in the compounds of the formula (I); i.e., n is zero.

In another embodiment of the present invention there are groups $X_i$ present and the total number of groups $X_i$ in the compound of the formula (I), i.e., the sum of the values for n, is up to sixteen, preferably three to ten, more preferably three to eight, and very preferably three to six.

In accordance with this embodiment, the alcohols in question are ethoxylated and/or propoxylated alcohols, preferably either exclusively ethoxylated or exclusively propoxylated alcohols, and more preferably exclusively ethoxylated alcohols.

To comply with this proviso, the number n for each k and each m independently of one another may be 0 or a positive number-for example, 0 to 10, preferably 1 to 5, more preferably 1 to 4, very preferably 1 to 3, and more particularly 1 to 2.

Examples of alcohols $R^a$—(—Y—[—$X_i$]$_n$—H)$_{(k+m)}$, in which Y is a nitrogen atom, are triethanolamine, tripropanolamine, and 1,3,5-tris(2-hydroxyethyl)cyanuric acid, preference being given to 1,3,5-tris(2-hydroxyethyl)cyanuric acid. In these cases, n is in each case 1 and $X_i$ in each case —$CH_2$—$CH_2$—O—, —$CH_2$—$CH(CH_3)$—O— or —$CH(CH_3)$—$CH_2$—O—.

The radical $R^b$ is derived from monomeric isophorone diisocyanate; in accordance with the invention it is relatively unimportant whether the urethane or allophanate group is attached to a primary or secondary carbon atom. Depending on reaction conditions (see below), a greater part of the urethane or allophanate groups will be attached to a secondary carbon atom. According to E. Spyrou, Farbe and Lack 106, 10/2006, pp. 126-130, for example, the selectivity of the allophanate reaction can be influenced by means of different catalysts.

The number-average molecular weight $M_n$ of the allophanate-group-containing polyisocyanates of the formula (I) is generally below 2000, preferably below 1800, more preferably below 1500, very preferably below 1200, and more particularly below 1100 g/mol.

The NCO content (calculated as NCO with a molar weight of 42 g/mol) is in general more than 5% by weight, preferably more than 6% by weight and more preferably more than 8% by weight and up to 17% by weight, preferably up to 15% by weight.

Besides allophanate groups, the allophanate-group-containing polyisocyanates of the invention may carry minor amounts of further reactive groups, examples being unreacted hydroxyl groups, and also isocyanurate groups.

The allophanate-group-containing polyisocyanates are prepared by reacting isophorone diisocyanate and the corresponding alkoxylated alcohol with one another, with or without solvent, under urethanizing conditions and then under allophanatizing conditions.

The temperature in this reaction is generally up to 150° C., preferably up to 120° C., more preferably below 100° C., and very preferably below 90° C., and it is usually carried out in the presence of at least one catalyst that catalyzes the urethanizing and/or allophanatizing reaction. The formation of the urethane groups can alternatively be carried out in the absence of a catalyst.

The temperature of the reaction ought in general to be at least 20° C., preferably at least 30, more preferably at least 40, and very preferably at least 50° C. In one preferred embodiment, the reaction temperature is at least 80° C.

Catalysts here are those compounds which, through their presence in a mixture of reactants, lead to a higher proportion of urethane or allophanate-group-containing reaction products than for the same mixture of reactants in their absence, under the same reaction conditions.

They are, for example, organic amines, more particularly tertiary aliphatic, cycloaliphatic or aromatic amines, and/or organometallic Lewis acid compounds. Organometallic Lewis acid compounds contemplated include, for example, tin compounds, such as, for example, tin(II) salts of organic carboxylic acids, e.g., tin(II) diacetate, tin(II) dioctoate, tin (II) bis(ethylhexanoate), and tin(II) dilaurate, and the dialkyltin(IV) salts of organic carboxylic acids, e.g., dimethyltin diacetate, dibutyltin diacetate, dibutyltin dibutyrate, dibutyltin bis(2-ethylhexanoate), dibutyltin dilaurate, dibutyltin maleate, dioctyltin dilaurate, and dioctyltin diacetate. It is also possible to use zinc(II) salts, such as, for example, zinc (II) dioctoate. Metal complexes as well, such as acetylacetonates of iron, titanium, aluminum, zirconium, manganese, nickel, zinc, and cobalt, are possible. Other metal catalysts are described by Blank et al. in Progress in Organic Coatings, 1999, Vol. 35, pages 19-29.

Preferred organometallic Lewis acid compounds are dimethyltin diacetate, dibutyltin dibutyrate, dibutyltin bis(2-ethylhexanoate), dibutyltin dilaurate, dioctyltin dilaurate, zinc (II) dioctoate, zirconium acetylacetonate, and zirconium 2,2, 6,6-tetramethyl-3,5-heptanedionate.

Bismuth catalysts and cobalt catalysts as well, and also cesium salts, can be used as catalysts. Suitable cesium salts include those compounds in which the following anions are used: F—, Cl—, ClO—, $ClO_3$—, $ClO_4$—, Br—, I—, $IO_3$—, CN—, OCN—, $NO_2$—, $NO_3$—, $HCO_3$—, $CO_3^{2-}$, $S^{2-}$, SH—, $HSO_3$—, $SO_3^{2-}$, $HSO_4$—, $SO_4^{2-}$, $S_2O_4^{2-}$, $S_2O_5^{2-}$, $S_2O_6^{2-}$, $S_2O_7^{2-}$, $S_2O_8^{2-}$, $H_2PO_2$—, $H_2PO_4$—, $HPO_4^{2-}$, $PO_4^{3-}$, $P_2O_7^{4-}$, $(OC_nH_{2n+1})$—, $(C_nH_{2n-1}O_2)$—, $(C_nH_{2n-3}O_2)^-$, and $(C_{n+1}H_{2n-2}O_4)^{2-}$, where n stands for the numbers 1 to 20.

Preference here is given to cesium carboxylates, in which the anion conforms to the formulae $(C_nH_{2n-1}O_2)^-$ and also $(C_{n+1}H_{2n-2}O_4)^{2-}$, with n being 1 to 20. Particularly preferred cesium salts have monocarboxylate anions of the general formula $(C_nH_{2n-1}O_2)^-$, where n stands for the numbers 1 to 20. Particularly noteworthy in this context are formate, acetate, propionate, hexanoate, and 2-ethylhexanoate.

As catalysts it is additionally possible to employ the following:

organic metal salts of the formula $(A)_n$-R—O—CO—$O^\ominus M^\oplus$, as per U.S. Pat. No. 3,817,939, in which:

A is a hydroxyl group or a hydrogen atom, n is a number from 1 to 3,

R is a polyfunctional linear or branched, aliphatic or aromatic hydrocarbon radical, and $M^\oplus$ is a cation, e.g., an alkali metal cation or a quaternary ammonium cation, such as tetraalkylammonium, and also quaternary hydroxyalkylammonium compounds of formula $$R^{24},R^{25},R^{26}N^\oplus—CH_2—CH(OH)—R^{27\ominus}O—(CO)—R^{28}$$

as catalyst as per DE-A-26 31 733 (U.S. Pat. No. 4,040,992) with the definitions stated therein for the radicals.

Particularly suitable as catalysts for the process are quaternary ammonium salts corresponding to the formula

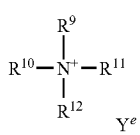

where
$Y^\ominus$=carboxylate ($R^{13}COO^-$), fluoride ($F^-$), carbonate ($R^{13}O(CO)O^-$) or hydroxide ($OH^-$),
as described for $Y^-=OH^-$ in U.S. Pat. No. 4,324,879 and in German Laid-Open Specifications 2,806,731 and 2,901,479.

The radical $Y^\ominus$ is preferably a carboxylate, carbonate or hydroxide and more preferably a carboxylate or hydroxide.

$R^{13}$ therein is hydrogen, $C_1$ to $C_{20}$ alkyl, $C_6$ to $C_{12}$ aryl or $C_7$ to $C_{20}$ arylalkyl, each of which may optionally be substituted.

Preferably $R^{13}$ is hydrogen or $C_1$ to $C_8$ alkyl.

Preferred quaternary ammonium salts are those in which the radicals $R^9$ to $R^{12}$ are like or different alkyl groups having 1 to 20, preferably 1 to 4, carbon atoms, which are optionally substituted by hydroxyl or phenyl groups.

Two of the radicals $R^9$ to $R^{12}$ may also combine with the nitrogen atom and, if desired, with a further nitrogen or oxygen atom to form a heterocyclic five-, six- or seven-membered ring. The radicals $R^9$ to $R^{11}$ may in each case also be ethylene radicals, which combine with the quaternary nitrogen atom and with a further, tertiary nitrogen atom to form a bicyclic triethylenediamine structure, subject to the proviso that the radical $R^{12}$ is then a hydroxyalkyl group having 2 to 4 carbon atoms, in which the hydroxyl group is located preferably in the 2-position relative to the quaternary nitrogen atom. The hydroxy-substituted radical or the hydroxy-substituted radicals may also contain other substituents, examples being $C_1$ to $C_4$ alkyloxy substituents.

The ammonium ions may also be part of a single-membered or multi-membered ring system, derived, for example, from piperazine, morpholine, piperidine, pyrrolidine, quinuclidine or 1,4-diazabicyclo[2.2.2]octane.

Examples of groups $R^9$ to $R^{12}$ having 1 to 20 carbon atoms are, independently of one another, methyl, ethyl, propyl, isopropyl, n-butyl, sec-butyl, tert-butyl, pentyl, hexyl, heptyl, octyl, 2-ethylhexyl, 2,4,4-trimethylpentyl, nonyl, isononyl, decyl, dodecyl, tetradecyl, hetadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, chloromethyl, 2-chloroethyl, trichloromethyl, trifluoromethyl, 1,1-dimethyl-2-chloroethyl, 2-methoxyisopropyl, 2-ethoxyethyl, 2-hydroxyethyl, 2-hydroxypropyl, 3-hydroxypropyl, 4-hydroxybutyl, 6-hydroxyhexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl, 6-ethoxyhexyl, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, methylnaphthyl, isopropylnaphthyl, chloronaphthyl, 2,6-dimethylphenyl, 2,4,6-trimethylphenyl, 2,6-dimethoxyphenyl, 2,6-dichlorophenyl, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, chlorocyclohexyl, dichlorocyclohexyl, dichlorocyclopentyl, norbornyl or norbornenyl.

Independently of one another, the radicals $R^9$ to $R^{12}$ are preferably $C_1$ to $C_4$ alkyl. $R^{12}$ may additionally be benzyl or a radical of the formula

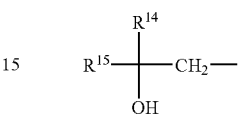

in which $R^{14}$ and $R^{15}$ independently of one another may be hydrogen or $C_1$ to $C_4$ alkyl.

Particularly preferred radicals $R^9$ to $R^{12}$ are, independently of one another, methyl, ethyl, and n-butyl, and for $R^{12}$ additionally benzyl, 2-hydroxyethyl, and 2-hydroxypropyl.

For the process of the invention it is possible with preference to use the following catalysts:

Quaternary ammonium hydroxides, preferably N,N,N-trimethyl-N-benzylammonium hydroxide and N,N,N-trimethyl-N-(2-hydroxypropyl)ammonium hydroxide, in accordance with DE-A-38 06 276.

Hydroxyalkyl-substituted quaternary ammonium hydroxides in accordance with EP-A-10 589 (U.S. Pat. No. 4,324,879).

Organic metal salts of the formula $(A)_n$-R—O—CO—$O^\ominus M^\oplus$ in accordance with U.S. Pat. No. 3,817,939, in which A is a hydroxyl group or a hydrogen atom, n is a number from 1 to 3, R is a polyfunctional linear or branched, aliphatic or aromatic hydrocarbon radical, and M is a cation of a strong base, e.g., an alkali metal cation or a quaternary ammonium cation, such as tetraalkylammonium.

Preferred catalysts are zinc(II) salts, and among them especially zinc acetylacetonate.

Additionally preferred are the stated cesium salts and bismuth salts.

With catalysts of these kinds it is possible to suppress the formation of polyisocyanates during the reaction. Accordingly it is possible to obtain reaction mixtures in which the ratio of allophanate groups to isocyanurate groups is at least 0.1:1, preferably at least 0.3:1, more preferably at least 0.5:1, very preferably at least 1:1, more particularly at least 1.5:1, especially at least 5:1, and even at least 10:1.

Additionally preferred is dibutyltin dilaurate.

Depending on activity, the catalyst is used normally in amounts of 0.001 to 10 mol % in respect of isocyanate groups employed, preferably 0.5 to 8, more preferably 1 to 7, and very preferably 2 to 5 mol %.

Isophorone diisocyanate is usually used in at least twice-equimolar stoichiometry relative to the hydroxyl groups in the alcohol, preferably in a 2.5-to 10-fold excess of isophorone diisocyanate to hydroxyl groups in one alcohol, preferably in a 3-to 8-fold excess, and more preferably in a 4-to 5-fold excess.

The unreacted portion of isophorone diisocyanate either may remain in the reaction mixture or, preferably, is separated off, preferably via a distillation, such as a flash or thin-film distillation, for example.

The amount of unreacted isophorone diisocyanate in the reaction mixture is generally below 1% by weight, preferably below 0.5% by weight, and more preferably below 0.3% by weight.

The reaction is carried out preferably without solvent, but may also be carried out in the presence of at least one solvent. Similarly, the resulting reaction mixture, after the end of the reaction, may be formulated in a solvent.

Solvents which can be employed are those which have no groups that are reactive toward isocyanate groups, and in which the polyisocyanates are soluble to an extent of at least 10% by weight, preferably at least 25%, more preferably at least 50%, very preferably at least 75%, more particularly at least 90%, and especially at least 95% by weight.

Examples of solvents of this kind are aromatic hydrocarbons (including alkylated benzenes and naphthalenes) and/or (cyclo)aliphatic hydrocarbons and mixtures thereof, chlorinated hydrocarbons, ketones, esters, alkoxylated alkyl alkanoates, ethers, and mixtures of the solvents.

Preferred aromatic hydrocarbon mixtures are those which comprise predominantly aromatic $C_7$ to $C_{14}$ hydrocarbons and may encompass a boiling range from 110 to 300° C.; particular preference is given to toluene, o-, m-or p-xylene, trimethylbenzene isomers, tetramethylbenzene isomers, ethylbenzene, cumene, tetrahydronaphthalene and mixtures comprising them.

Examples thereof are the Solvesso® products from ExxonMobil Chemical, especially Solvesso® 100 (CAS No. 64742-95-6, predominantly $C_9$ and $C_{10}$ aromatics, boiling range about 154-178° C.), 150 (boiling range about 182-207° C.), and 200 (CAS No. 64742-94-5), and also the Shellsol® products from Shell, Caromax® (e.g., Caromax® 18) from Petrochem Carless and Hydrosol from DHC (e.g., as Hydrosol® A 170). Hydrocarbon mixtures comprising paraffins, cycloparaffins, and aromatics are also available commercially under the names Kristalloel (for example, Kristalloel 30, boiling range about 158-198° C. or Kristalloel 60: CAS No. 64742-82-1), white spirit (for example likewise CAS No. 64742-82-1) or solvent naphtha (light: boiling range about 155-180° C., heavy: boiling range about 225-300° C.). The aromatics content of such hydrocarbon mixtures is generally more than 90%, preferably more than 95%, more preferably more than 98%, and very preferably more than 99% by weight. It may be advisable to use hydrocarbon mixtures having a particularly reduced naphthalene content.

Examples of (cyclo)aliphatic hydrocarbons include decalin, alkylated decalin, and isomer mixtures of linear or branched alkanes and/or cycloalkanes.

The amount of aliphatic hydrocarbons is generally less than 5%, preferably less than 2.5%, and more preferably less than 1% by weight.

Esters are, for example, n-butyl acetate, ethyl acetate, 1-methoxyprop-2-yl acetate, and 2-methoxyethyl acetate.

Ethers are, for example, THF, dioxane, and also the dimethyl, diethyl or di-n-butyl ethers of ethylene glycol, diethylene glycol, triethylene glycol, propylene glycol, dipropylene glycol or tripropylene glycol.

Ketones are, for example, acetone, diethyl ketone, ethyl methyl ketone, isobutyl methyl ketone, methyl amyl ketone, and tert-butyl methyl ketone.

The allophanate-group-containing polyisocyanates of the invention find application, for example, in two-component polyurethane coating materials having at least one component comprising isocyanate-reactive groups (binder). For this purpose they can be used alone or in a mixture with polyisocyanates other than these allophanate-group-containing polyisocyanates as a crosslinker component.

Such other polyisocyanates are obtainable by oligomerization of monomeric isocyanates.

The monomeric isocyanates used may be aromatic, aliphatic or cycloaliphatic, preferably aliphatic or cycloaliphatic, which is referred to for short in this text as (cyclo)aliphatic; aliphatic isocyanates are particularly preferred.

Aromatic isocyanates are those which comprise at least one aromatic ring system, in other words not only purely aromatic compounds but also araliphatic compounds.

Cycloaliphatic isocyanates are those which comprise at least one cycloaliphatic ring system.

Aliphatic isocyanates are those which comprise exclusively linear or branched chains, i.e., acyclic compounds.

The monomeric isocyanates are preferably diisocyanates, which carry precisely two isocyanate groups. They can, however, in principle also be monoisocyanates, having one isocyanate group.

In principle, higher isocyanates having on average more than 2 isocyanate groups are also contemplated. Suitability therefor is possessed for example by triisocyanates, such as triisocyanatononane, 2,4,6-triisocyanatotoluene, triphenylmethane triisocyanate or 2,4,4'-triisocyanatodiphenyl ether, or the mixtures of diisocyanates, triisocyanates, and higher polyisocyanates that are obtained, for example, by phosgenation of corresponding aniline/formaldehyde condensates and represent methylene-bridged polyphenyl polyisocyanates.

These monomeric isocyanates do not contain any substantial products of reaction of the isocyanate groups with themselves.

The monomeric isocyanates are preferably isocyanates having 4 to 20 C atoms. Examples of typical diisocyanates are aliphatic diisocyanates such as tetramethylene diisocyanate, pentamethylene 1,5-diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, trimethylhexane diisocyanate or tetramethylhexane diisocyanate, cycloaliphatic diisocyanates such as 1,4-, 1,3- or 1,2-diisocyanatocyclohexane, 4,4'-or 2,4'-di(isocyanatocyclohexyl)methane, 1-isocyanato-3,3,5-trimethyl-5-(isocyanatomethyl)cyclohexane (isophorone diisocyanate), 1,3-or 1,4-bis(isocyanatomethyl)cyclohexane or 2,4-, or 2,6-diisocyanato-1-methylcyclohexane, and also 3 (or 4), 8 (or 9)-bis(isocyanatomethyl)tricyclo[$5.2.1.0^{2.6}$]decane isomer mixtures, and also aromatic diisocyanates such as tolylene 2,4-or 2,6-diisocyanate and the isomer mixtures thereof, m-or p-xylylene diisocyanate, 2,4'-or 4,4'-diisocyanatodiphenylmethane and the isomer mixtures thereof, phenylene 1,3-or 1,4-diisocyanate, 1-chlorophenylene 2,4-diisocyanate, naphthylene 1,5-diisocyanate, diphenylene 4,4'-diisocyanate, 4,4'-diisocyanato-3,3'-dimethylbiphenyl, 3-methyldiphenylmethane 4,4'-diisocyanate, tetramethylxylylene diisocyanate, 1,4-diisocyanatobenzene or diphenyl ether 4,4'-diisocyanate.

Particular preference is given to hexamethylene 1,6-diisocyanate, 1,3-bis(isocyanatomethyl)cyclohexane, isophorone diisocyanate, and 4,4'-or 2,4'-di(isocyanatocyclohexyl)methane, very particular preference to isophorone diisocyanate and hexamethylene 1,6-diisocyanate, and especial preference to hexamethylene 1,6-diisocyanate.

Mixtures of said isocyanates may also be present.

Isophorone diisocyanate is usually in the form of a mixture, specifically a mixture of the cis and trans isomers, generally in a proportion of about 60:40 to 80:20 (w/w), preferably in a proportion of about 70:30 to 75:25, and more preferably in a proportion of approximately 75:25.

Dicyclohexylmethane 4,4'-diisocyanate may likewise be in the form of a mixture of the different cis and trans isomers.

For the present invention it is possible to use not only those diisocyanates obtained by phosgenating the corresponding amines but also those prepared without the use of phosgene, i.e., by phosgene-free processes. According to EP-A-0 126 299 (U.S. Pat. No. 4,596,678), EP-A-126 300 (U.S. Pat. No. 4,596,679), and EP-A-355 443 (U.S. Pat. No. 5,087,739), for example, (cyclo)aliphatic diisocyanates, such as hexamethylene 1,6-diisocyanate (HDI), isomeric aliphatic diisocyanates having 6 carbon atoms in the alkylene radical, 4,4'-or 2,4'-di(isocyanatocyclohexyl)methane, and 1-isocyanato-3-isocyanatomethyl-3,5,5-trimethylcyclohexane (isophorone diisocyanate or IPDI) can be prepared by reacting the (cyclo) aliphatic diamines with, for example, urea and alcohols to give (cyclo)aliphatic biscarbamic esters and subjecting said esters to thermal cleavage into the corresponding diisocyanates and alcohols. The synthesis takes place usually continuously in a circulation process and in the presence, if desired, of N-unsubstituted carbamic esters, dialkyl carbonates, and other by-products recycled from the reaction process. Diisocyanates obtained in this way generally contain a very low or even unmeasurable fraction of chlorinated compounds, which is advantageous, for example, in applications in the electronics industry.

In one embodiment of the present invention the isocyanates used have a total hydrolyzable chlorine content of less than 200 ppm, preferably of less than 120 ppm, more preferably less than 80 ppm, very preferably less than 50 ppm, in particular less than 15 ppm, and especially less than 10 ppm. This can be measured by means, for example, of ASTM specification D4663-98. Of course, though, monomeric isocyanates having a higher chlorine content can also be used, of up to 500 ppm, for example.

It will be appreciated that it is also possible to employ mixtures of those monomeric isocyanates which have been obtained by reacting the (cyclo)aliphatic diamines with, for example, urea and alcohols and cleaving the resulting (cyclo) aliphatic biscarbamic esters, with those diisocyanates which have been obtained by phosgenating the corresponding amines.

The polyisocyanates which can be formed by oligomerizing the monomeric isocyanates are generally characterized as follows:

The average NCO functionality of such compounds is in general at least 1.8 and can be up to 8, preferably 2 to 5, and more preferably 2.4 to 4.

The isocyanate group content after oligomerization, calculated as NCO=42 g/mol, is generally from 5% to 25% by weight unless otherwise specified.

The polyisocyanates other than the allophanate-group-containing polyisocyanates according to the invention are preferably compounds as follows:

1) Polyisocyanates containing isocyanurate groups and derived from aromatic, aliphatic and/or cycloaliphatic diisocyanates. Particular preference is given in this context to the corresponding aliphatic and/or cycloaliphatic isocyanatoisocyanurates and in particular to those based on hexamethylene diisocyanate and isophorone diisocyanate. The isocyanurates present are, in particular, trisisocyanatoalkyl and/or trisisocyanatocycloalkyl isocyanurates, which constitute cyclic trimers of the diisocyanates, or are mixtures with their higher homologs containing more than one isocyanurate ring. The isocyanatoisocyanurates generally have an NCO content of 10% to 30% by weight, in particular 15% to 25% by weight, and an average NCO functionality of 2.6 to 8.

2) Polyisocyanates containing uretdione groups and having aromatically, aliphatically and/or cycloaliphatically attached isocyanate groups, preferably aliphatically and/or cycloaliphatically attached, and in particular those derived from hexamethylene diisocyanate or isophorone diisocyanate. Uretdione diisocyanates are cyclic dimerization products of diisocyanates. The polyisocyanates containing uretdione groups are obtained in the context of this invention as a mixture with other polyisocyanates, more particularly those specified under 1). For this purpose the diisocyanates can be reacted under reaction conditions under which not only uretdione groups but also the other polyisocyanates are formed, or the uretdione groups are formed first of all and are subsequently reacted to give the other polyisocyanates, or the diisocyanates are first reacted to give the other polyisocyanates, which are subsequently reacted to give products containing uretdione groups.

3) Polyisocyanates containing biuret groups and having aromatically, cycloaliphatically or aliphatically attached, preferably cycloaliphatically or aliphatically attached, isocyanate groups, especially tris(6-isocyanatohexyl)biuret or its mixtures with its higher homologs. These polyisocyanates containing biuret groups generally have an NCO content of 18% to 22% by weight and an average NCO functionality of 2.8 to 6.

4) Polyisocyanates containing urethane and/or allophanate groups and having aromatically, aliphatically or cycloaliphatically attached, preferably aliphatically or cycloaliphatically attached, isocyanate groups, such as may be obtained, for example, by reacting excess amounts of diisocyanate, such as of hexamethylene diisocyanate or of isophorone diisocyanate, with mono- or polyhydric alcohols (A). These polyisocyanates containing urethane and/or allophanate groups generally have an NCO content of 12% to 24% by weight and an average NCO functionality of 2.5 to 4.5. Polyisocyanates of this kind containing allophanate and/or allophanate groups may be prepared without catalyst or, preferably, in the presence of catalysts, such as ammonium carboxylates or ammonium hydroxides, for example, or allophanatization catalysts, such as Zn(II) compounds, for example, in each case in the presence of monohydric, dihydric or polyhydric, preferably monohydric, alcohols.

5) Polyisocyanates comprising oxadiazinetrione groups, derived preferably from hexamethylene diisocyanate or isophorone diisocyanate. Polyisocyanates of this kind comprising oxadiazinetrione groups are accessible from diisocyanate and carbon dioxide.

6) Polyisocyanates comprising iminooxadiazinedione groups, derived preferably from hexamethylene diisocyanate or isophorone diisocyanate. Polyisocyanates of this kind comprising iminooxadiazinedione groups are preparable from diisocyanates by means of specific catalysts.

7) Uretonimine-modified polyisocyanates.
8) Carbodiimide-modified polyisocyanates.
9) Hyperbranched polyisocyanates, of the kind known for example from DE-A1 10013186 or DE-A1 10013187.
10) Polyurethane-polyisocyanate prepolymers, from di- and/or polyisocyanates with alcohols.
11) Polyurea-polyisocyanate prepolymers.

12) The polyisocyanates 1)-11), preferably 1), 3), 4), and 6), can be converted, following their preparation, into polyisocyanates containing biuret groups or urethane/allophanate groups and having aromatically, cycloaliphatically or aliphatically attached, preferably (cyclo)aliphatically attached, isocyanate groups. The formation of biuret groups, for example, is accomplished by addition of water or by reaction with amines. The formation of urethane and/or allophanate groups is accomplished by reaction with monohydric, dihydric or polyhydric, preferably monohydric, alcohols, in the presence if desired of suitable catalysts. These polyisocyanates containing biuret or urethane/allophanate groups generally have an NCO content of 18% to 22% by weight and an average NCO functionality of 2.8 to 6.

13) Hydrophilically modified polyisocyanates, i.e., polyisocyanates which as well as the groups described under 1-12 also comprise groups which result formally from addition of molecules containing NCO-reactive groups and hydrophilicizing groups to the isocyanate groups of the above molecules. The latter groups are nonionic groups such as alkylpolyethylene oxide and/or ionic groups derived from phosphoric acid, phosphonic acid, sulfuric acid or sulfonic acid, and/or their salts.

14) Modified polyisocyanates for dual cure applications, i.e., polyisocyanates which as well as the groups described under 1-12 also comprise groups resulting formally from addition of molecules containing NCO-reactive groups and UV-crosslinkable or actinic-radiation-crosslinkable groups to the isocyanate groups of the above molecules. These molecules are, for example, hydroxyalkyl (meth)acrylates and other hydroxyvinyl compounds.

The diisocyanates or polyisocyanates recited above may also be present at least partly in blocked form.

Classes of compounds used for blocking are described in D. A. Wicks, Z. W. Wicks, Progress in Organic Coatings, 36, 148-172 (1999), 41, 1-83 (2001) and also 43, 131-140 (2001).

Examples of classes of compounds used for blocking are phenols, imidazoles, triazoles, pyrazoles, oximes, N-hydroxyimides, hydroxybenzoic esters, secondary amines, lactams, CH-acidic cyclic ketones, malonic esters or alkyl acetoacetates.

In one preferred embodiment of the present invention the polyisocyanate is selected from the group consisting of isocyanurates, biurets, urethanes, and allophanates, preferably from the group consisting of isocyanurates, urethanes, and allophanates, more preferably from the group consisting of isocyanurates and allophanates; in particular it is a polyisocyanate containing isocyanurate groups.

In one particularly preferred embodiment the polyisocyanate encompasses polyisocyanates comprising isocyanurate groups and obtained from 1,6-hexamethylene diisocyanate and/or isophorone diisocyanate.

In one further particularly preferred embodiment the polyisocyanate encompasses a mixture of polyisocyanates comprising isocyanurate groups and obtained from 1,6-hexamethylene diisocyanate and from isophorone diisocyanate.

In one particularly preferred embodiment the polyisocyanate is a mixture comprising low-viscosity polyisocyanates, preferably polyisocyanates comprising isocyanurate groups, having a viscosity of 600-1500 mPa*s, more particularly below 1200 mPa*s, low-viscosity urethanes and/or allophanates having a viscosity of 200-1600 mPa*s, more particularly 600-1500 mPa*s, and/or polyisocyanates comprising iminooxadiazinedione groups.

In this specification, unless noted otherwise, the viscosity is reported at 23° C. in accordance with DIN EN ISO 3219/A.3 in a cone/plate system with a shear rate of 1000 s$^{-1}$.

The allophanate-group-containing polyisocyanates of the invention may if desired be used in a mixture with other polyisocyanates, as crosslinker components, with at least one binder in polyurethane coating materials.

Generally speaking, for polyisocyanate compositions, in other words the sum of the compounds containing isocyanate groups,
50% to 100% by weight of the allophanate-group-containing polyisocyanates of the invention are used, preferably 50% to 90% by weight, and more preferably 60% to 80% by weight, and
0% to 50% by weight of other polyisocyanates, preferably 10% to 50%, more preferably 20% to 40% by weight,
with the proviso that the sum is always 100% by weight.

The binders may be, for example, polyacrylate polyols, polyester polyols, polyether polyols, polyurethane polyols; polyurea polyols; polyester-polyacrylate polyols; polyester-polyurethane polyols; polyurethane-polyacrylate polyols, polyurethane-modified alkyd resins; fatty acid-modified polyester-polyurethane polyols, copolymers with allyl ethers, graft polymers of the stated groups of compounds having, for example, different glass transition temperatures, and also mixtures of the stated binders. Preference is given to polyacrylate polyols, polyester polyols, and polyether polyols.

Preferred OH numbers, measured in accordance with DIN 53240-2, are 40-350 mg KOH/g resin solids for polyesters, preferably 80-180 mg KOH/g resin solids, and 15-250 mg KOH/g resin solids for polyacrylateols, preferably 80-160 mg KOH/g.

Additionally the binders may have an acid number in accordance with DIN EN ISO 3682 of up to 200 mg KOH/g, preferably up to 150 and more preferably up to 100 mg KOH/g.

Polyacrylate polyols preferably have a molecular weight $M_n$ of at least 1000, more preferably at least 2000, and very preferably at least 5000 g/mol. The molecular weight $M_n$ may in principle have no upper limit, and may preferably be up to 200 000, more preferably up to 100 000, very preferably up to 80 000, and more particularly up to 50 000 g/mol.

The latter may be, for example, monoesters of α,β-unsaturated carboxylic acids, such as acrylic acid, methacrylic acid (identified for short in this specification as "(meth)acrylic acid"), with diols or polyols which have preferably 2 to 20 C atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,4-butanediol, 1,5-pentanediol, neopentyl glycol, neopentyl glycol hydroxypivalate, 2-ethyl-1,3-propanediol, 2-methyl-1,3-propanediol, 2-butyl-2-ethyl-1,3-propanediol, 1,6-hexanediol, 2-methyl-1,5-pentanediol, 2-ethyl-1,4-butanediol, 2-ethyl-1,3-hexanediol, 2,4-diethyloctane-1,3-diol, 2,2-bis(4-hydroxycyclohexyl)propane, 1,1-, 1,2-, 1,3-and 1,4-bis(hydroxymethyl)cyclohexane, 1,2-, 1,3-or 1,4-cyclohexanediol, glycerol, trimethylolethane, trimethylolpropane, trimethylolbutane, pentaerythritol, ditrimethylolpropane, dipentaerythritol, sorbitol, mannitol, diglycerol, threitol, erythritol, adonitol (ribitol), arabitol (lyxitol), xylitol, dulcitol (galactitol), maltitol, isomalt, polyTHF with a molar weight between 162 and 4500, preferably 250 to 2000, poly-1,3-propanediol or polypropylene glycol with a molar weight between 134 and 2000, or polyethylene glycol with a molar weight between 238 and 2000.

Preference is given to 2-hydroxyethyl acrylate, 2-hydroxyethyl methacrylate, 2-or 3-hydroxypropyl acrylate, 1,4-butanediol monoacrylate or 3-(acryloyloxy)-2-hydroxypropyl acrylate, and particular preference to 2-hydroxyethyl acrylate and/or 2-hydroxyethyl methacrylate.

The hydroxyl-bearing monomers are used in the copolymerization in a mixture with other polymerizable monomers, preferably free-radically polymerizable monomers, preferably those composed to an extent of more than 50% by weight of $C_1$-$C_{20}$, preferably $C_1$ to $C_4$ alkyl (meth)acrylate, (meth) acrylic acid, vinylaromatics having up to 20 C atoms, vinyl esters of carboxylic acids comprising up to 20 C atoms, vinyl halides, nonaromatic hydrocarbons having 4 to 8 C atoms and 1 or 2 double bonds, unsaturated nitriles, and mixtures thereof. Particular preference is given to the polymers composed to an extent of more than 60% by weight of $C_1$-$C_{10}$ alkyl (meth)acrylates, styrene and its derivatives, vinylimidazole or mixtures thereof.

In addition the polymers may contain hydroxy-functional monomers corresponding to the above hydroxyl group content and, if desired, further monomers, examples being (meth) acrylic acid glycidyl epoxy esters, ethylenically unsaturated acids, more particularly carboxylic acids, acid anhydrides or acid amides.

Further polymers are, for example, polyesterols, as are obtainable by condensing polycarboxylic acids, especially dicarboxylic acids, with polyols, especially diols. In order to ensure a polyester polyol functionality that is appropriate for the polymerization, use is also made in part of triols, tetrols, etc, and also triacids etc.

Polyester polyols are known for example from Ullmanns Encyklopädie der technischen Chemie, 4th edition, volume 19, pp. 62 to 65. It is preferred to use polyester polyols which are obtained by reacting dihydric alcohols with dibasic carboxylic acids. In lieu of the free polycarboxylic acids it is also possible to use the corresponding polycarboxylic anhydrides or corresponding polycarboxylic esters of lower alcohols or mixtures thereof to prepare the polyester polyols. The polycarboxylic acids may be aliphatic, cycloaliphatic, aromatic or heterocyclic and may if desired be substituted, by halogen atoms for example, and/or unsaturated. Examples thereof that may be mentioned include the following:

Oxalic acid, maleic acid, fumaric acid, succinic acid, glutaric acid, adipic acid, sebacic acid, dodecanedioic acid, o-phthalic acid, isophthalic acid, terephthalic acid, trimellitic acid, azelaic acid, 1,4-cyclohexanedicarboxylic acid or tetrahydrophthalic acid, suberic acid, azelaic acid, phthalic anhydride, tetrahydrophthalic anhydride, hexahydrophthalic anhydride, tetrachlorophthalic anhydride, endomethylenetetrahydrophthalic anhydride, glutaric anhydride, maleic anhydride, dimeric fatty acids, their isomers and hydrogenation products, and also esterifiable derivatives, such as anhydrides or dialkyl esters, $C_1$-$C_4$ alkyl esters for example, preferably methyl, ethyl or n-butyl esters, of the stated acids are employed. Preference is given to dicarboxylic acids of the general formula HOOC—$(CH_2)_y$—COON, where y is a number from 1 to 20, preferably an even number from 2 to 20, and more preferably succinic acid, adipic acid, sebacic acid, and dodecanedicarboxylic acid.

Suitable polyhydric alcohols for preparing the polyesterols include 1,2-propanediol, ethylene glycol, 2,2-dimethyl-1,2-ethanediol, 1,3-propanediol, 1,2-butanediol, 1,3-butanediol, 1,4-butanediol, 3-methylpentane-1,5-diol, 2-ethylhexane-1, 3-diol, 2,4-diethyloctane-1,3-diol, 1,6-hexanediol, polyTHF having a molar mass of between 162 and 4500, preferably 250 to 2000, poly-1,3-propanediol having a molar mass between 134 and 1178, poly-1,2-propanediol having a molar mass between 134 and 898, polyethylene glycol having a molar mass between 106 and 458, neopentyl glycol, neopentyl glycol hydroxypivalate, 2-ethyl-1,3-propanediol, 2-methyl-1,3-propanediol, 2,2-bis(4-hydroxycyclohexyl)propane, 1,1-, 1,2-, 1,3-and 1,4-cyclohexanedimethanol, 1,2-, 1,3-or 1,4-cyclohexanediol, trimethylolbutane, trimethylolpropane, trimethylolethane, neopentyl glycol, pentaerythritol, glycerol, ditrimethylolpropane, dipentaerythritol, sorbitol, mannitol, diglycerol, threitol, erythritol, adonitol (ribitol), arabitol (lyxitol), xylitol, dulcitol (galactitol), maltitol or isomalt, which if desired may have been alkoxylated as described above.

Preferred alcohols are those of the general formula HO—$(CH_2)_x$—OH, where x is a number from 1 to 20, preferably an even number from 2 to 20. Preferred are ethylene glycol, butane-1,4-diol, hexane-1,6-diol, octane-1,8-diol and dodecane-1,12-diol. Additionally preferred is neopentyl glycol.

Also suitable, furthermore, are polycarbonate diols of the kind obtainable, for example, by reacting phosgene with an excess of the low molecular mass alcohols specified as synthesis components for the polyester polyols.

Also suitable are lactone-based polyester diols, which are homopolymers or copolymers of lactones, preferably hydroxy-terminated adducts of lactones with suitable difunctional starter molecules. Suitable lactones are preferably those which derive from compounds of the general formula HO—$(CH_2)_z$—COON, where z is a number from 1 to 20 and where one H atom of a methylene unit may also have been substituted by a $C_1$ to $C_4$ alkyl radical. Examples are ε-caprolactone, β-propiolactone, gamma-butyrolactone and/or methyl-ε-caprolactone, 4-hydroxybenzoic acid, 6-hydroxy-2-naphthoic acid or pivalolactone, and mixtures thereof. Examples of suitable starter components include the low molecular mass dihydric alcohols specified above as a synthesis component for the polyester polyols. The corresponding polymers of ε-caprolactone are particularly preferred. Lower polyester diols or polyether diols as well can be used as starters for preparing the lactone polymers. In lieu of the polymers of lactones it is also possible to use the corresponding, chemically equivalent polycondensates of the hydroxycarboxylic acids corresponding to the lactones.

Also suitable as polymers, furthermore, are polyetherols, which are prepared by addition reaction of ethylene oxide, propylene oxide or butylene oxide with H-active components. Polycondensates of butanediol are also suitable.

In addition it is possible to use hydroxy-functional carboxylic acids, such as dimethylolpropionic acid or dimethylolbutanoic acid, for example.

The polymers can of course also be compounds containing primary or secondary amino groups.

For this purpose, polyisocyanate composition and binder are mixed with one another in a molar ratio of isocyanate groups to isocyanate-reactive groups of 0.1:1 to 10:1, preferably 0.2:1 to 5:1, more preferably 0.3:1 to 3:1, very preferably 0.5:1 to 2:1, more particularly 0.8:1 to 1.2:1, and especially 0.9:1 to 1.1:1, it being possible if desired to mix in further, typical coatings constituents, and the resulting mixture is applied to the substrate.

Subsequently the coating-material mixture is cured under suitable conditions. Depending on application, this may take place, for example, at 100 to 140° C., in the case for example of coating materials in OEM applications, or in a lower temperature range of 20 to 80° C., for example.

Depending on temperature, this usually takes not more than 12 hours, preferably up to 8 hours, more preferably up to 6, very preferably up to 4, and in particular up to 3 hours.

It is additionally possible for coating compositions to comprise 0% to 10% by weight of at least one UV stabilizer.

Suitable stabilizers comprise typical UV absorbers such as oxanilides, triazines, and benzotriazole (the latter available as Tinuvin® grades from Ciba-Spezialitätenchemie), and benzophenones.

They may further comprise 0% to 5% by weight of suitable free-radical scavengers, examples being sterically hindered amines such as 2,2,6,6-tetramethylpiperidine, 2,6-di-tert-butylpiperidine or derivatives thereof, e.g., bis(2,2,6,6-tetramethyl-4-piperidyl) sebacate.

Furthermore, coating compositions may further comprise 0% to 10% by weight of further, typical coatings additives.

Further, typical coatings additives that can be used include, for example, antioxidants, activators (accelerants), fillers, pigments, dyes, antistatic agents, flame retardants, thickeners, thixotropic agents, surface-active agents, viscosity modifiers, plasticizers or chelating agents.

Suitable thickeners, in addition to free-radically (co)polymerized (co)polymers, include typical organic and inorganic thickeners such as hydroxymethylcellulose or bentonite.

Chelating agents which can be used include, for example, ethylenediaminoacetic acid and salts thereof, and also β-diketones.

Suitable fillers comprise silicates, examples being silicates obtainable by hydrolysis of silicon tetrachloride, such as Aerosil® from Degussa, siliceous earth, talc, aluminum silicates, magnesium silicates, calcium carbonates, etc.

The substrates are coated by typical methods known to the skilled worker, with at least one coating composition being applied in the desired thickness to the substrate to be coated, and any volatile constituents of the coating composition being removed, if desired with heating. This operation may if desired be repeated one or more times. Application to the substrate may take place in a known way, as for example by spraying, troweling, knifecoating, brushing, rolling, rollercoating, flowcoating, laminating, injection backmolding or coextruding.

The thickness of a film of this kind for curing may be from 0.1 μm up to several mm, preferably from 1 to 2000 μm, more preferably 5 to 200 μm, very preferably from 5 to 60 μm (based on the coating material in the state in which the solvent has been removed from the coating material).

Additionally provided by the present invention are substrates coated with a coating material comprising the allophanate-group-containing polyisocyanates of the invention.

Polyurethane coating materials of this kind are especially suitable for applications requiring particularly high application reliability, exterior weathering resistance, optical qualities, solvent resistance, chemical resistance, and water resistance.

The two-component coating compositions and coating formulations obtained are in principle suitable for coating substrates such as wood, wood veneer, paper, cardboard, paperboard, textile, film, leather, nonwoven, plastics surfaces, glass, ceramic, mineral building materials, such as molded cement blocks and fiber-cement slabs, or metals, which in each case may optionally have been precoated or pretreated. With particular preference, however, they are suitable for the coating of plastics surfaces and metallic substrates.

These coating compositions are used preferably as clearcoat, basecoat, and topcoat(s), primers and surfacers, and in particular they are suitable, on account of their high scratch resistance, as topcoat material, preferably as clearcoat material, more particularly in coatings on (large) vehicles and aircraft, and in automobile finishes as OEM and refinish.

It is an advantage of the allophanate-group-containing polyisocyanates of the invention that in clearcoats they produce high hardness in conjunction with good elasticity. Moreover, the products of the invention usually result in a high functionality.

EXAMPLES

Example 1

800 g of monomeric isophorone diisocyanate (3.6 mol) were admixed with 47.9 g (0.18 mol) of propoxylated glycerol which carries on average one propylene oxide group per hydroxyl group, and this mixture was heated to 80° C. The clear solution was admixed with 0.2 g of zinc acetylacetonate. The mixture was held at 120° C. for approximately five hours. The NCO content was 30.6%. The mixture was admixed with 0.2 ml of diethylhexyl phosphate. Unreacted monomer was removed in a thin-film evaporator at an external temperature of 165° C. and at 4.1 mbar.

The NCO content of the solid product was 13.2%. A 70% strength solution of the product in butyl acetate had an NCO content of 10.4% and a viscosity of 2340 mPas.

Comparative Example 1

800 g (4.76 mol) of 1,6-hexamethylene diisocyanate were admixed with 63.3 g (9.24 mol) of the same propoxylated glycerol as in example 1, and the mixture was heated to 80° C. The clear solution was admixed with 0.2 g of zinc acetylacetonate. The mixture was heated to 120° C.

After an hour the contents of the flask had undergone crosslinking.

Use examples:

The polyisocyanate from example 1, and also a comparative polyisocyanate (mixture of a commercial isocyanurate based on 1,6-hexamethylene diisocyanate (NCO content about 22.0% by weight, viscosity according to DIN EN ISO 3219 at 23° C. and 1000 s$^{-1}$ about 3300 mPas, Basonat® HI 100 from BASF AG, Ludwigshafen) and a commercial isocyanurate based on isophorone diisocyanate (NCO content about 12.0% by weight, 70% strength in butyl acetate, viscosity in accordance with DIN EN ISO 3219 at 23° C. and 1000 s$^{-1}$ about 700 mPas, Basonat® IT 170 B from BASF AG, Ludwigshafen)) in a stoichiometric ratio of 7:3), were mixed with a hydroxy-functional polyacrylate resin (Macrynal® SM 600, Cytec; solids content=60%; OH number=100 mg KOH/g), corresponding to a stoichiometric NCO/OH ratio of 1:1, and adjusted with butyl acetate to an application viscosity of 20 s (DIN 53 211 cup 4 mm efflux nozzle). Using a drawing frame, coatings with a wet film thickness of 200 μm were applied to metal panels. After a 10-minute flash-off time, the resulting clearcoats were cured at 80° C. and 130° C. respectively for 30 minutes, and measurements were made of the pendulum hardness and the Erichsen cupping of the coating materials. The investigations of the coating properties took place after 24 hours of storage of the coated panels in a controlled-climate chamber at 23° C. and 50% relative humidity.

The Erichsen cupping was determined in the same way as in DIN 53156. High values denote high flexibility.

The pendulum hardness was determined in the same way as in DIN 53157, with high values denoting high hardness.

|  | Pendulum hardness 80° C. | Erichsen cupping 80° C. |
| --- | --- | --- |
| Comparative polyisocyanate | 118 | >9.0 |
| Example 1 | 135 | >9.0 |

|  | Pendulum hardness 130° C. | Erichsen cupping 130° C. |
| --- | --- | --- |
| Comparative polyisocyanate | 128 | >9.0 |
| Example 1 | 140 | 8.5 |

The experiments show that the inventive polyisocyanates have a comparable elasticity to that exhibited by the comparative polyisocyanate mixture, with improved hardness.

The invention claimed is:

1. An allophanate-group-comprising polyisocyanate represented by formula (I)

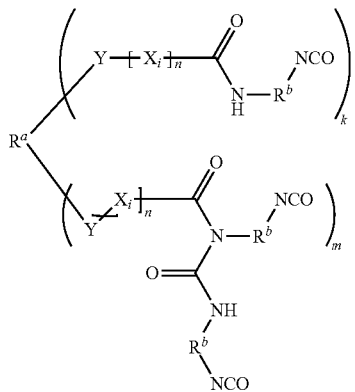

wherein $R^a$ is a (k+m)-valent radical, k is 0 or a positive number, m is a positive number, whereby (k +m) together add up to a positive number of at least 3, Y is an oxygen or a nitrogen atom, $X_i$, for each i from 1 to n, independently of one another, is selected from the group consisting of —C(CH$_3$)$_2$—CH$_2$—O—, —CH$_2$—CHVin—O—, —CHVin—CH$_2$—O—, —CH$_2$—CHPh—O— and —CHPh—CH$_2$—O—, wherein Ph is phenyl and Vin is vinyl, n for each k and each m, independent of one another, is 1 to 5, and $R^b$ for each k and each m, independent of one another, is a radical

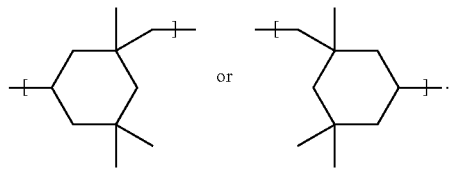

2. The allophanate-group-comprising polyisocyanate of claim 1, wherein (k+m) takes on a value of 3 to 4.

3. The allophanate-group-comprising polyisocyanate of claim 1, which is obtained from an alcohol $R^a$—(—Y—H)$_{(k+m)}$, in which Y is an oxygen atom, and is selected from the group consisting of trimethylolbutane, trimethylolpropane, trimethylolethane, pentaerythritol, glycerol, ditrimethylolpropane, dipentaerythritol, sorbitol, mannitol, diglycerol, threitol, erythritol, adonitol (ribitol), arabitol (lyxitol), xylitol, and dulcitol (galactitol).

4. The allophanate-group-comprising polyisocyanate of claim 1, which is obtained from a compound $R^a$—(—Y—[—$X_i$]$_n$—H)$_{(k+m)}$ and is selected from the group consisting of triethanolamine, tripropanolamine, and 1,3,5-tris(2-hydroxyethyl)cyanuric acid.

5. The allophanate-group-comprising polyisocyanate of claim 1, wherein the NCO content, calculated as NCO with a molar weight of 42 g/mol, is more than 5% by weight and up to 17% by weight.

6. A two-component polyurethane coating material comprising at least one allophanate-group-comprising polyisocyanate of claim 1, optionally, at least a second polyisocyanate, and at least one component which comprises at least one isocyanate-reactive group.

7. A method of producing a clearcoat material, comprising adding an allophanate-group-comprising polyisocyanate of claim 1 to a clearcoat material precursor.

8. A method of producing a coating composition for large vehicle, aircraft, and automobile finish as OEM and refinish, comprising adding an allophanate-group-comprising polyisocyanate of claim 1 to a coating composition precursor.

9. A process for preparing an allophanate-group-comprising polyisocyanate of claim 1, said process comprising mixing isophorone diisocyanate with an alcohol, in at least twice-equimolar stoichiometry relative to hydroxyl groups in the alcohol, and reacting the isophorone diisocyanate and the alcohol together in the presence of at least one catalyst at a temperature of at least 80° C.

10. The process of claim 9, wherein the at least one catalyst is at least one selected from the group consisting of a zinc salt, a cesium salt, a bismuth salt, and a tin compound.

11. The allophanate-group-comprising polyisocyanate of claim 1, wherein m >k.

12. The allophanate-group-comprising polyisocyanate of claim 1, wherein m≧(k+1).

13. The allophanate-group-comprising polyisocyanate of claim 1, wherein k≦0.5.

14. The allophanate-group-comprising polyisocyanate of claim 1, wherein k ≦0.2.

15. The allophanate-group-comprising polyisocyanate of claim 1, wherein k =0.

16. The allophanate-group-comprising polyisocyanate of claim 1, wherein the total number of $X_i$ groups is 3 to 6.

* * * * *